(12) United States Patent
Abenaim et al.

(10) Patent No.: US 8,379,797 B2
(45) Date of Patent: Feb. 19, 2013

(54) POWER MANAGEMENT OF CT SYSTEMS

(75) Inventors: Daniel Abenaim, Lynnfield, MA (US);
Adrian Delforge, Rockport, MA (US)

(73) Assignee: Analogic Corporation, Peabody, MA (US)

(*) Notice: Subject to any disclaimer, the term of this patent is extended or adjusted under 35 U.S.C. 154(b) by 245 days.

(21) Appl. No.: 12/845,988

(22) Filed: Jul. 29, 2010

(65) Prior Publication Data
US 2012/0027161 A1 Feb. 2, 2012

(51) Int. Cl.
*H05G 1/24* (2006.01)
(52) U.S. Cl. ...................................... 378/103
(58) Field of Classification Search ............... 378/4, 15, 378/101, 103, 104
See application file for complete search history.

(56) References Cited

U.S. PATENT DOCUMENTS

| 4,912,735 A | 3/1990 | Beer |
| RE34,379 E | 9/1993 | Gordon |
| 5,808,376 A | 9/1998 | Gordon et al. |
| 7,522,705 B2 * | 4/2009 | Katcha et al. ................. 378/103 |
| 7,634,046 B2 | 12/2009 | Krumme |
| 7,717,619 B2 * | 5/2010 | Katcha et al. ................. 378/197 |

* cited by examiner

*Primary Examiner* — Jurie Yun
(74) *Attorney, Agent, or Firm* — Cooper Legal Group LLC

(57) ABSTRACT

One or more techniques and/or systems described herein implement, among other things, an energy storage component disposed in a stationary portion (e.g., non-rotating portion) of a CT scanning apparatus. The energy storage component receives electrical power from an external source, such as a power outlet, and stores the electrical power. The stored electrical power is provided for an operation on a rotating portion (e.g., non-stationary) of the CT scanning apparatus upon demand, and is sufficient to perform the operation alone or in combination with power from the external source.

20 Claims, 6 Drawing Sheets

POWER MANAGEMENT OF CT SYSTEMS

BACKGROUND

The present application relates to the field of radiographic imaging. It finds particular application with the provision of electrical power for computed tomography (CT) scanners, a line scanner, or other radiography imaging system (e.g., mammography system, general radiology system, etc).

Radiographic imaging systems, such as computed tomography (CT) systems, line scanners, etc., provide information, or images, of an object under examination (e.g., interior aspects of an object under examination). Generally, the object is exposed to radiation, and one or more images are formed based upon the radiation absorbed by the object, or rather an amount of radiation that is able to pass through the object. Typically, highly dense objects absorb (e.g., attenuate) more radiation than less dense objects, and thus an object having a higher density, such as a bone or gun, for example, will be apparent when surrounded by less dense objects, such as fatty tissue or clothing, for example. A detector array, generally positioned opposite a radiation source from which radiation is emitted relative the object under examination, is configured to detect radiation that traverses the object under examination and convert such radiation into signals and/or data that may be processed to produce the image(s). Such an image(s) may be viewed by security personnel to detect threat items (e.g., weapons, etc.) and/or viewed by medical personnel to detect medical condition (e.g., cancerous tissue).

In some scanners, such as three-dimensional imaging scanners (e.g., CT scanners), for example, the detector array and radiation source are mounted on opposing sides of a rotating gantry that forms a ring, or donut, around the object under examination. In such a scanner, the rotating gantry (including the radiation source and/or detector array) is rotated in a circle situated within an x, y plane about an axis extending in the z-dimension (e.g., an "isocenter") during an examination. The object is generally supported by a support article (e.g., a bed, conveyor belt, etc.) that runs in the z-direction substantially parallel to the mechanical center of rotation (e.g., the isocenter). As the rotating gantry is rotated, radiation is substantially continuously emitted from a focal spot of the radiation source toward the object under examination.

Medical CT systems typically utilize a large amount of power for a short period of time (periodic duty cycle), unlike security-based CT systems, which typically utilize less power relatively continuously. A medical CT scanner typically utilizes a large amount of power while the X-ray tube is on, for example, from 30 to 100 kW for a scan. This amount of electrical power cannot be provided by the standard single phase mains power receptacle, which typically provides up to four kW of service.

Traditionally, this high power, periodic duty cycle requirement calls for using a three-phase power line installation that is capable of providing the power continuously even though it is merely used in bursts. A dedicated, three-phase power connection is often made to satisfy the momentary demand, thereby requiring a special connection, and availability of three-phase service. However, some parts of the world cannot meet the power line stability required and special power regulators must be installed, such as for the three-phase service. This type of siting requirement can be expensive, may be limited, and can deny CT technology in smaller settings. Further, if the CT apparatus is connected to a dedicated line its portability is limited.

However the duty cycle of a CT scanner is low (periodic), particularly in a medical-type operation. For example, for medical CT scanning, a patient is typically brought into a room where the scan is performed, and then another patient is brought in, where a period of time elapses between scans. Therefore, even though the energy requirements for a medical-type CT scan are high, the duty cycle is low and intermittent, providing a time between uses where energy could be stored for use during a scan. Previously, battery systems were installed on the rotating gantry side of the CT apparatus. However, this arrangement limited the choice of batteries, limited power capabilities, and required the whole power chain to rotate. This made for a lot of weight to be accommodated and balanced on the rotating side, making the CT machines costly and difficult to set up.

SUMMARY

Aspects of the present application address the above matters, and others. According to one aspect, a computed tomography (CT) scanning apparatus is provided. The CT scanning apparatus comprises an energy storage component that is disposed in a stationary portion (e.g., non-rotating portion) of the CT scanner. The energy storage component is configured to receive electrical power from an external source, store the electrical power, and provide the stored electrical power for an operation on a rotating portion (e.g., non-stationary) of the CT scanning apparatus upon demand. The stored electrical power provided by the energy storage component comprises power sufficient to perform the operation.

According to another aspect, a method is provided for providing electrical power for an operation on a rotating portion of a computed tomography (CT) scanning apparatus. The method comprises directing electrical power from an external source to an energy storage component disposed in a stationary portion of the CT scanning apparatus. Further, electrical power is stored in the energy storage component, where the stored electrical power is sufficient to perform the operation on the rotating portion of the CT scanning apparatus. Additionally, the stored electric power is provided upon demand for the operation.

According to yet another aspect, a radiography scanning apparatus is provided. The radiography scanning apparatus comprises a rotating portion, which comprises a radiation source that emits radiation as at least part of a scan operation; and a detector array that detects the emitted radiation during the scan operation. The radiography scanning apparatus further comprises a stationary portion, which comprises an energy storage component. The energy storage component is configured to store electrical power from an external source that is applied to the energy storage component during a charge period, where the electrical power from the external source is not sufficient to perform the scan operation on the rotating portion alone. Additionally, the energy storage component is configured to provide the stored electrical power for the scan operation on the rotating portion of the radiography scanning apparatus upon demand, where a combination of electrical power from the energy storage component and the external source is sufficient to perform the scan operation on the rotating portion.

FIGURES

The application is illustrated by way of example and not limitation in the figures of the accompanying drawings, in which like references indicate similar elements and in which.

DESCRIPTION

Figure 1:
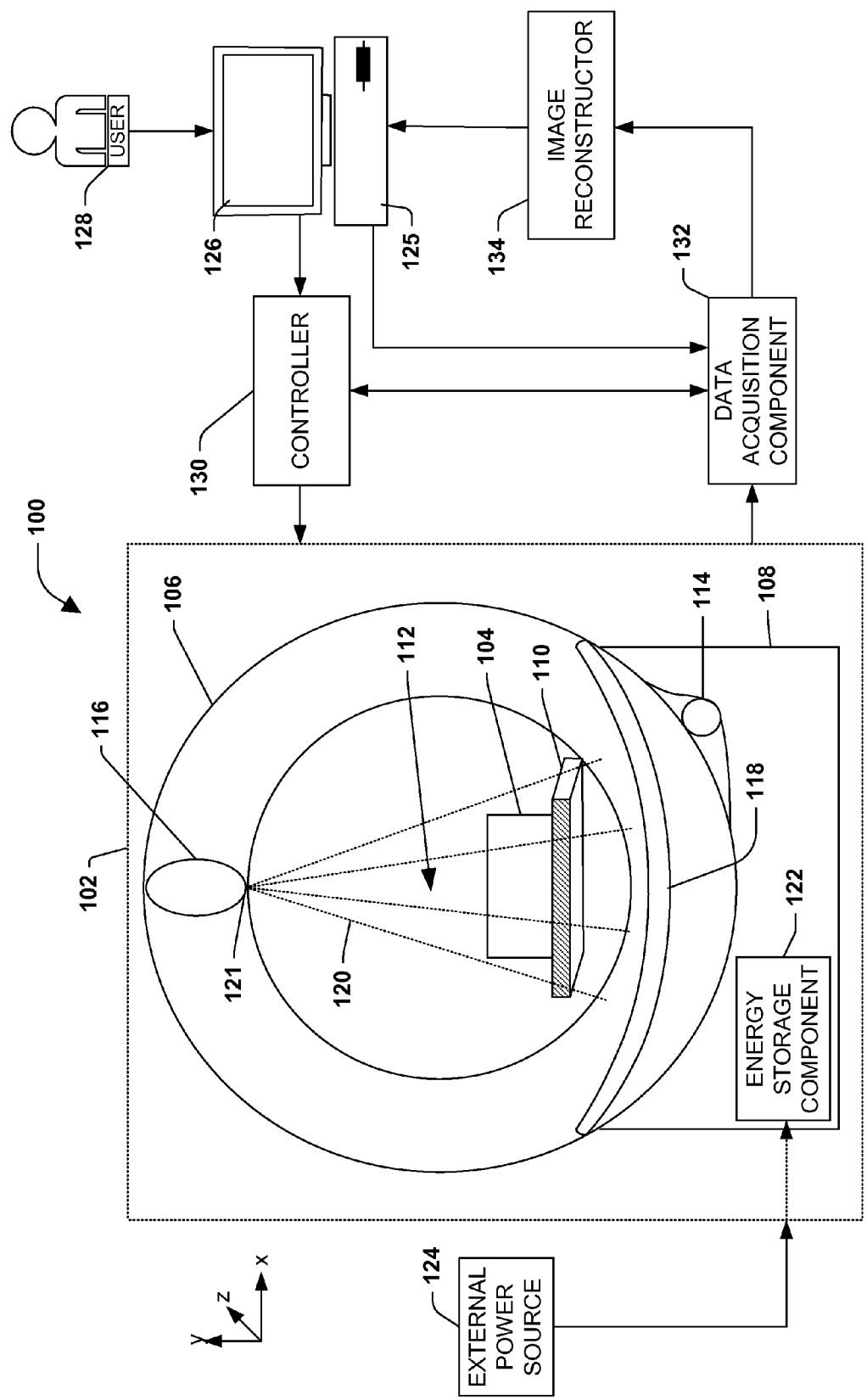
FIG. 1 is a schematic block diagram illustrating an example of a CT scanner.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

FIG. 1 is an illustration of an example environment 100 in which data that is generated from components comprised within a rotating gantry 106 of a radiography scanner (e.g., a CT scanner) may be acquired so that one or more images of an object 104 under examination may be produced and displayed on a monitor 126, for example, such as for viewing by a human user 128. Such a scanner may be used to identify a tumor in a human patient at a medical center or in an animal at a veterinary clinic, and/or to identify objects of interest (e.g., potential threat objects, banned objects) associated with (e.g., comprising, comprised within, etc.) an object 104 (e.g., luggage) under examination at a security checkpoint, for example. In another embodiment, no image is generated, but a density (or some other object property) of respective objects (or aspects or parts thereof) can be identified and compared with a list of densities associated with predetermined items (e.g., banned items) to determine if the object 104 potentially comprises one or more of the predetermined items.

In the example environment 100, the scanner comprises an object scanning apparatus 102 configured to examine one or more objects 104 (e.g., a human patient, a series of suitcases at an airport, etc.). The object scanning apparatus 102 can comprise the rotating gantry 106 (e.g., rotating portion of the scanning apparatus) and a stationary gantry 108 (e.g., stationary portion of the scanning apparatus). During an examination of the object(s) 104, the object(s) 104 can be placed on a support article 110, such as a bed or conveyor belt, that is selectively positioned in an examination region 112 (e.g., a hollow bore in the rotating gantry portion 106), and the rotating gantry 106 can be rotated about the object(s) 104 by a rotator 114 (e.g., motor, drive shaft, chain, etc.).

The rotating gantry 106 may surround a portion of the examination region 112 and comprises a radiation source 116 (e.g., an ionizing x-ray source) and a detector array 118 that is mounted on a substantially diametrically opposite side of the rotating gantry 106 relative to the radiation source 116 (e.g., where a focal spot 121 of the radiation source 116 would generally serve as a center of the detector array 118 should the detector array completely encircle the radiation source 116).

During an examination of the object(s) 104, the radiation source 116 emits radiation 120 towards the object(s) 104 under examination while the rotating gantry 106 (including the radiation source 116 and detector array 118) rotates about the object(s) 104. Generally, in a CT scanner, the radiation 120 is emitted substantially continuously during the examination. However, in some CT scanners and/or in other radiography scanners, the radiation 120 may be emitted intermittently during the rotation.

As the radiation 120 traverses the object(s) 104, the radiation 120 may be attenuated differently by different aspects of the object(s) 104. Because different aspects attenuate different percentages of the radiation 120, an image may be reconstructed based upon the attenuation, or rather the variations in the number of photons that are detected by the detector array 118. For example, more dense aspects of the object(s) 104, such as a bone or metal plate, may attenuate more of the radiation 120 (e.g., causing fewer photons to strike the detector array 118) than less dense aspects, such as skin or clothing.

In some embodiments, while the object(s) 104 is being scanned, or examined, the object(s) 104 may be translated along an axis traveling in the z-dimension (if, as illustrated, the rotating gantry 106 is configured to rotate in an x, y plane). In this way, an object that has a z-dimension greater than the z-dimension of the radiation traversing the object may be scanned more quickly (relative to a step-and-shoot scanning approach). It will be appreciated that if the object(s) 104 is being translated (e.g., in the z direction) during a scan while the rotating gantry 106 is rotating (e.g., in the x, y plane), the scan may be referred to as a helical or spiral scan.

Radiation 120 that impinges the detector array 118 generally creates an electrical charge that may be detected by one or more pixels, or elements, of the detector array 118 that are in close spatial proximity to the location where the radiation impinged. Respective pixels generate an analog signal (in a linear format) indicative of the electrical charge detected (e.g., generated by photodiodes in the detector array 118), and such signals are fed to a data acquisition component 122. Because the electrical charge detected by the one or more pixels is directly related to the number of photons (e.g., an electrical charge of 1.2 keV may be equivalent to one photon), the output is indicative of the attenuation of the radiation 120 as it traversed the object(s) 104. It will be appreciated that, in one embodiment, when a pixel is not detecting electrical charge, the pixel can emit an analog, baseline signal that indicates that the pixel has detected little to no electrical charge.

It will be understood to those skilled that in some embodiments, an analog to digital (A/D) signal converter (not shown, but generally operably coupled with or comprised within the detector array 118 and/or the data acquisition component 132) may be configured to receive the analog signals and convert the signals into digital signals, such as by using digital timing comparison of the incoming signal to a known signal. The data acquisition component 132 is configured to prepare the output signals, in projection space, for an image reconstruction component 134. In one embodiment, configuring the output signals for reconstruction can comprise remapping (also referred to herein as converting or encoding) the output signals from a first format to a second format that is more suitable for reconstruction from projection space to image space, for example.

In the example environment 100, signal data from the data acquisition component 132 is transmitted to an image reconstructor 134 configured to receive the projection space data, for example. The image reconstructor 134 is configured to reconstruct one or more images of the object 104 under examination using analytic, iterative, or other image reconstruction techniques known to those skilled in the art (e.g., 2D filtered back projection). In this way, the data is converted from projection space to image space, a domain that may be more understandable by a user 128 viewing the image(s), for example.

The example environment 100 also includes a terminal 125 (e.g., a computer) configured to receive the image(s), which can be displayed on a monitor 126 of the terminal 125 to a user 128 (e.g., security personnel, medical personnel, etc.). In this way, a user 128 can inspect the image(s) to identify areas of interest within the object(s) 104. The terminal 125 can also be configured to receive user input which can direct the object scanning apparatus 102 how to operate (e.g., a speed to rotate, a speed of a conveyor belt, etc.) and/or can direct the terminal 125 to display an image of the object(s) 104 from a particular angle, for example.

In the example environment 100, a controller 130 is operably coupled to the terminal 125. In one example, the controller 130 is configured to receive user input from the terminal 125 and generate instructions for the object scanning apparatus 102 indicative of operations to be performed. For example, the user 128 may want to rescan the object(s) 104, and the controller 130 may issue an instruction instructing the support article 110 to reverse direction (e.g., bringing the object(s) 104 back into an examination region 112 of the object scanning apparatus 102).

In the example environment 100, an external power source 124 (e.g., external to the scanning apparatus 102) provides electrical power to the scanning apparatus 102, for example, for operating the rotator 114, the x-ray source 116, and/or other components utilizing electrical power in the stationary portion 108 and rotating portion 106 of the scanning apparatus 102. The external power source, such as an electrical outlet providing power from a source electrical mains (e.g., from a grid service), can also provide electrical power to an energy storage component 122, which is described in more detail below. In this example, 100, the energy storage component is comprised in the stationary portion 108 of the scanning apparatus, such as to provide electrical power to the stationary portion 108 and rotating portion 106 of the scanning apparatus 102. It will be appreciated, however, that some or all of the energy storage component may be external to the stationary portion 108 of the scanning apparatus 102 and/or external to the scanning apparatus 102 as well.

Figure 2:
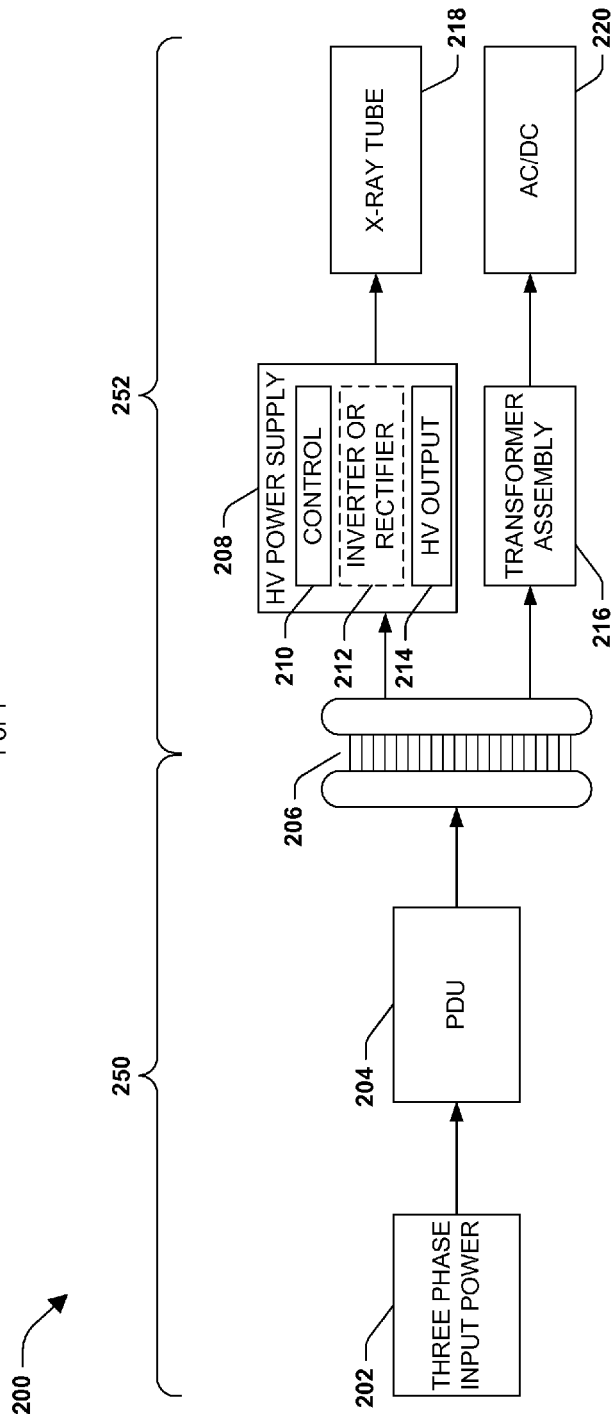
FIG. 2 is a component diagram illustrating power supply in a conventional CT scanner.

FIG. 2 is a component diagram illustrating an example embodiment 200 of one or more portions of existing technology for providing electrical power to a rotating portion of a computed tomography (CT) apparatus. A three-phase electrical supply 202 provides input electrical power for the CT apparatus. For example, CT imaging typically utilizes electrical power resources that may not be available from a single-phase mains supply, such as for generating x-rays from a radiation emitter (e.g., for medical diagnosis) as described above. Therefore, in this example, a three-phase service is utilized to take advantage of a higher voltage (e.g., 200/400 VAC) and power level associated with three-phase electrical distribution.

When power is called for by the CT apparatus a power distribution unit 204 (PDU), comprised on a non-rotating portion 250 of the CT apparatus, receives the three-phase electrical power service, conditions the electric power appropriately, and provides it to a contact slip-ring 206. For example, the PDU 204 may comprise a matching/isolation transformer.

The contact slip-ring 206 provides an electrical connection from a non-rotating portion 250 (e.g., stationary portion, such as 108 of FIG. 1) to a rotating portion 252 (e.g., 106 of FIG. 1) of the CT apparatus. For example, electrical connectors, such as brushes or springs, connected to a first side of the slip ring remain in contact with a second side of the slip ring while at least the rotating portion rotates, thereby providing continuous electrical connectivity.

A high voltage power supply (HVPS) unit 208 located in the rotating portion 252 of the CT apparatus receives the electrical power from the contact slip ring 206. Electrical power traversing the contact slip ring 206 can be AC or DC depending on, among other things, external source input power 202 and power needs for the x-ray tube 218. For example, where the input power 202 comprises three-phase AC and the x-ray tube 218 utilizes DC, a rectifier 212 may be present on the rotating portion 252 to convert the AC from the slip ring 206 to DC for the x-ray tube 218. Alternately, in another embodiment, an inverter 212 may be present on the rotating side 252 to convert DC to AC, such as for the x-ray tube 218. It will be appreciated that a variety of combinations of inverters and/or rectifiers can be present on the non-rotating portion 250 and/or the rotating portion 252 to provide appropriate current for operations in the CT apparatus.

A control component 210 can be present in the HV power supply, and may be used to manage power demands, for example, for the x-ray tube 218. For example, when power is needed for a CT scan, the control component 210 can call for an appropriate amount of power to charge the x-ray tube 218 to emit radiation for the scan. Further, the electrical power can go through the inverter or rectifier 212 to a high voltage output component 214, which supplies the needed power for the x-ray tube to emit a sufficient amount of radiation for a CT scan, for example.

Additionally, the rotating portion 252 of the example embodiment 200 can comprise auxiliary components, such as photon detectors, computer controls, alignment controls, etc., which utilize electrical power. Electrical power can be provided across the contact slip ring 206 to a transformer assembly 216, which can condition the incoming electrical power to appropriate levels for a variety of components. In some embodiments, depending on the component served, the conditioned electrical power may be converted, at 220, from AC to DC by, among other things, rectifiers, and/or from DC to AC by, among other things, inverters.

Figure 3:
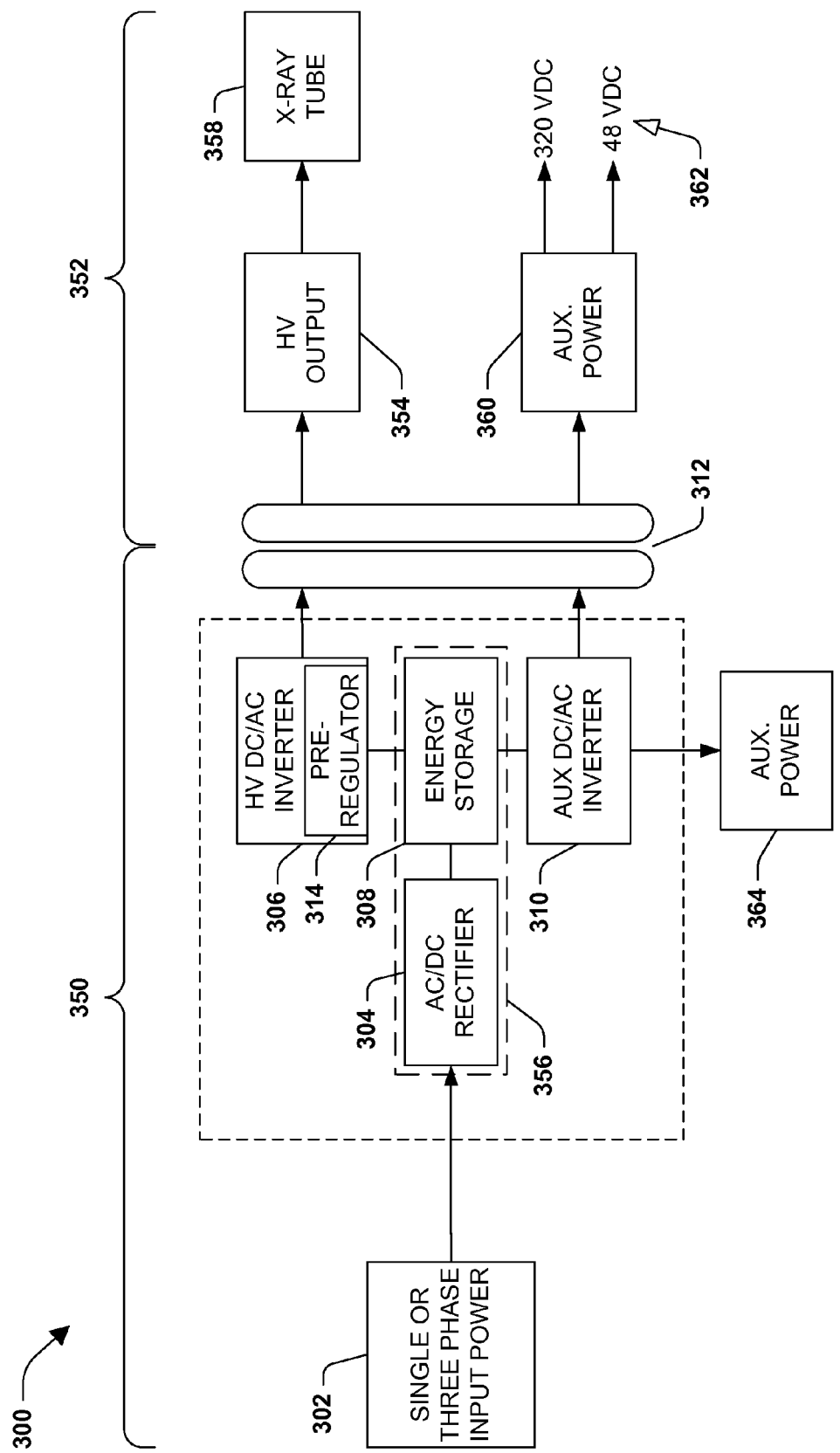
FIG. 3 is a component diagram illustrating an example implementation of an energy storage component as provided herein.

FIG. 3 is a component diagram of an example system 300 comprising one or more portions of a computed tomography (CT) scanning apparatus with an energy storage component 308 as provided herein. The energy storage component 308 is disposed in a stationary portion 350 of the CT scanner (e.g., 102 of FIG. 1). The energy storage component 308 receives electrical power supplied from an external source 302, such as a single phase or three phase input power source (e.g., one or more electrical outlets or dedicated power sources).

For example, the CT scanner may comprise a power supply line that merely plugs into an existing mains supply outlet (e.g., a standard U.S. 120 volt or 240 volt electrical outlet). As another example, the CT scanner may comprise a dedicated power supply line that is connected with a three-phase power supply. In another embodiment, the CT scanner may be connected to a plurality of power supply lines. For example, a first power supply line may supply power for the energy storage component and/or for powering direct scanning operations (e.g., x-ray tube, detectors, rotator); and a second power supply line may supply power for auxiliary systems, such as computing systems.

Further, the energy storage component 308 stores electrical power, such as in one or more batteries configured to store electrical energy, and/or one or more capacitors configured to store electrical energy. For example, a secondary-type battery (e.g., rechargeable battery) may store input electrical power from the external source 302. As another example, a capacitor (e.g., alone or in combination with one or more batteries) may store input electrical power from the external source 302.

Additionally, the energy storage component 308 provides the stored electrical power for an operation on a rotating portion 352 (e.g., the gantry 106 of FIG. 1) of the CT scanning apparatus upon demand. The stored electrical power provided by the energy storage component 308 is sufficient to perform one or more operations on the rotating portion 352. For example, a control unit (not shown) on the rotating portion 352 may request (e.g., demand) power for generating x-rays using an x-ray tube 358, such as to perform a scan of an object.

In one embodiment, the stored electrical power provided by the energy storage component 308 can also be sufficient to perform one or more operations on the non-rotating portion 350 of the CT apparatus. For example, for a CT scanning operation, as described above, a plurality pixel elements can detect photons during a scan and the detected photons can be used to compile a CT image. In this example, computing and compilation of the image, or portions thereof, may be performed in the stationary portion, where electrical power to perform the operation can be provided by the energy storage component 308. As another example, energy storage component 308 can be utilized by a rotator (e.g., 114 of FIG. 1) on the stationary portion 350 to rotate the gantry (e.g., 106 of FIG. 1) for the rotating portion 352.

In yet another embodiment, the stored electrical power provided by the energy storage component 308 can be combined with electrical power provided from the external source 302 to perform one or more operations on the rotating portion, and/or the non-rotating portion of the CT apparatus. For example, the external source 302 may comprise a single-phase outlet that can provide merely four kW of electrical power. Further, in this example, the x-ray tube may require forty-five kW of electrical power to charge and emit sufficient radiation for a CT scanning operation. In this embodiment, the energy storage component 308 can be configured to store sufficient power to make up a difference between the external source 302 input (e.g., 4 kW) and a demanded power supply (e.g., 45 kW), such that when the electrical power provided by the energy storage component 308 is combined with electrical power provided from the external source 302 the combination meets the demand for the operation on the CT apparatus.

In one aspect, CT scanners typically utilize an electrical service that provides a greater level of electrical power than may be available through a common mains supply (e.g., residential electrical service). In one embodiment, as described above, the CT scanner can be connected to a dedicated, three-phase electrical service that provides sufficient power for generating x-rays for a typical CT scan. Further, in one embodiment, CT scanners are commonly used in a medical setting, where they have a periodic duty cycle. That is, for example, the scanner is used intermittently (e.g., instead of continuously) for respective patients subjected to the medical scans.

CT scanners used in a medical-type setting can utilize more electrical power than some other applications (e.g., security scanning of luggage) as a greater amount of x-rays are emitted by the radiation source during a medical scan. In one embodiment, the systems described herein may be utilized with a CT scanner that has a periodic duty-cycle, such as in medical imaging, where a greater amount of x-ray radiation is used intermittently. That is, for example, in a medical CT scanning setting patients are typically transported to the CT scanning area, a series of scans are performed and after some time another patient is brought in for scanning.

In this aspect, in one embodiment, the periodic nature of the duty-cycle can provide a "recharge time" for the energy storage component such as 308. In this way, for example, if a single phase "mains" power supply is used for the external source it may not be capable of providing sufficient electrical power for the x-ray tube in a medical setting (e.g., typically needing three-phase power). However, in this example, the energy storage component can be charged to a level that comprises sufficient electrical power to be able to provide the power needed to charge the x-ray tube for medical scanning (e.g., 45 kW). Therefore, in this embodiment, the CT scanning apparatus may be merely plugged into a common wall outlet, for example, to perform medical scanning, which provides for portability and/or use in areas that may not have three-phase power or reliable power supplies. It will be appreciated that this further utility and/or mobility of a CT scanning system afforded by the inclusion of an energy storage component 308 is not limited to medical applications, but extends to other applications as well (e.g., security scanning).

In the example system 300, the CT scanning apparatus can comprise an inverter 306, 310 that converts direct current (DC) from the energy storage component 308 to alternating current (AC) for the operation (e.g., scan, gantry rotation, computation, etc.). In one embodiment, a high voltage (HV) inverter 306 may be used to convert DC electrical power provided by the energy storage component 308 to AC electrical power. For example, the x-ray tube 358 may use up to 45 kW of AC power for generating radiation during a scanning operation at around 70 kilovolts (kV). In this example, the HV inverter 306 can provide AC power for the HV output component 354 on the rotating portion 352, for output to the x-ray tube 358.

In one embodiment, the inverter 306 can comprise a pre-regulation component 314 that boosts voltage from the energy storage component 308 above a desired threshold for the operation. In this embodiment, the preregulation component 314 can step up the voltage to a constant level for the inverter. In one embodiment, an H-bridge circuit may be utilized in the preregulation component 314, and a transformer in the preregulation component 314 can be decoupled in the H-bridge in order to provide a constant voltage.

As an example, using the preregulation component 314 may allow a constant voltage to be provided to the inverter 306 as the voltage from the energy storage component varies as energy is drawn (reduced) from the energy storage component. In one embodiment, the inverter 306, 310 can be disposed in the stationary portion 350 of the CT scanner between the energy storage component 308 and an electrical connection (e.g., 312) to the rotating portion 352 of the CT scanning apparatus. In this embodiment, where the energy storage component 308 comprises capacitors, for example, by allowing more electrical power to be drawn from the energy storage component 308 a size of the energy storage component can be reduced on the stationary portion 350, and the capacitors may be more efficiently utilized.

In the example system 300, an auxiliary inverter 310 can be coupled with the energy storage component 308 to convert DC to AC for auxiliary components of the CT scanner. For example, auxiliary components on the stationary portion 350 may be coupled with an auxiliary power component 364 that conditions and provides appropriate electrical power levels (e.g., transforms voltage, converts AC to DC) to various components on the stationary portion 350 (e.g., computing components, imaging components, rotator motor, examination surface motor, etc.). Further, for example, auxiliary components on the rotating portion 352 may be coupled with an auxiliary power component 360 that conditions and provides appropriate electrical power levels 362 to various components on the rotating portion 352, such as for rotating the gantry, operating the detector array, operating data acquisition components, etc.

In one embodiment, a non-contacting power transmission rotary component 312 is disposed between the stationary 350 and rotating 352 portions of the CT scanning apparatus, in order to provide a conduit for electrical power to the rotating portion 352 of the CT scanning apparatus. The non-contacting power transmission rotary component 312 does not utilize contact brushes or springs to make an electrical contact between two sides, although contact slip-rings may be used for connecting the two sides in one embodiment. Instead, for example, high-frequency (e.g., 80-100 kHz) AC power can be transported across a gap in the non-contacting power transmission rotary component 312.

In one embodiment, the HV inverter 306, which is operably coupled with the non-contacting power transmission rotary component 312, comprises a transformer that provides voltage at the appropriate level and frequency, as described above. In this way, for example, the non-contacting power transmission rotary component 312 can be utilized, which allows for the transformer to be placed on the stationary portion 350 (e.g., and made smaller) instead of the rotating portion 352, allowing the rotating portion to be less bulky and lighter (e.g., having less mass/inertia and requiring less energy to move/rotate).

In one embodiment, a rectifier component 304 is disposed between the external source 302 and the energy storage component 308. The rectifier component 304 conditions the electrical power from the external source 302 for storage in the energy storage component 308. That is, for example, the rectifier can convert AC electrical power from the external source 302 to DC electrical power for storage in the energy storage component 308, such as in batteries and/or capacitors.

In one embodiment, the rectifier component 304 may comprise a booster rectifier (e.g., a boost power factor correction component) that can convert current from AC to DC and provide an increase in the current output, such as to provide a stable input level for the energy storage component 308. For example, if the energy storage component comprises batteries for storing electrical power a desired incoming current level is used so that the batteries may be fully charged. In this example, the boost rectifier can boost the incoming current at or above the desired level so that the batteries may be more efficiently utilized (e.g., fully charged).

In one aspect, the rectifier (or boost rectifier) can be combined with the energy storage component 308 to provide a power line stabilizer 356. For example, the external source may not always provide stable or consistent electrical power, such as during electrical brownouts, line fluctuations, or in regions with unreliable power sources. In one embodiment, the power line stabilizer 356 can account for electrical service irregularities by temporarily storing electrical power in inductors for capacitors, for example, and releasing stored power to make up for detected power deficiencies/irregularities. Further, a pre-regulation component (not shown) in the power-line stabilizer 356 can mitigate electrical power spikes, for example, by stepping down the current if necessary. It will be appreciated that one or more of the components described herein as being comprised on the stationary side of the system 300 may also be external to the stationary side 350 and/or system 300. For example, some or all of the energy storage component 308 may be comprised of a bank of batteries and/or capacitors that are external to the stationary side 350 and/or system 300 where the bank is operatively (e.g., electrically) coupled to one or more other components within the system 300. This may provide for additional flexibility of the system, for example, (e.g., additional supplemental power if the input power supply 302 is interrupted, easier access to batteries for maintenance/replacement purposes, etc.).

Figure 4:
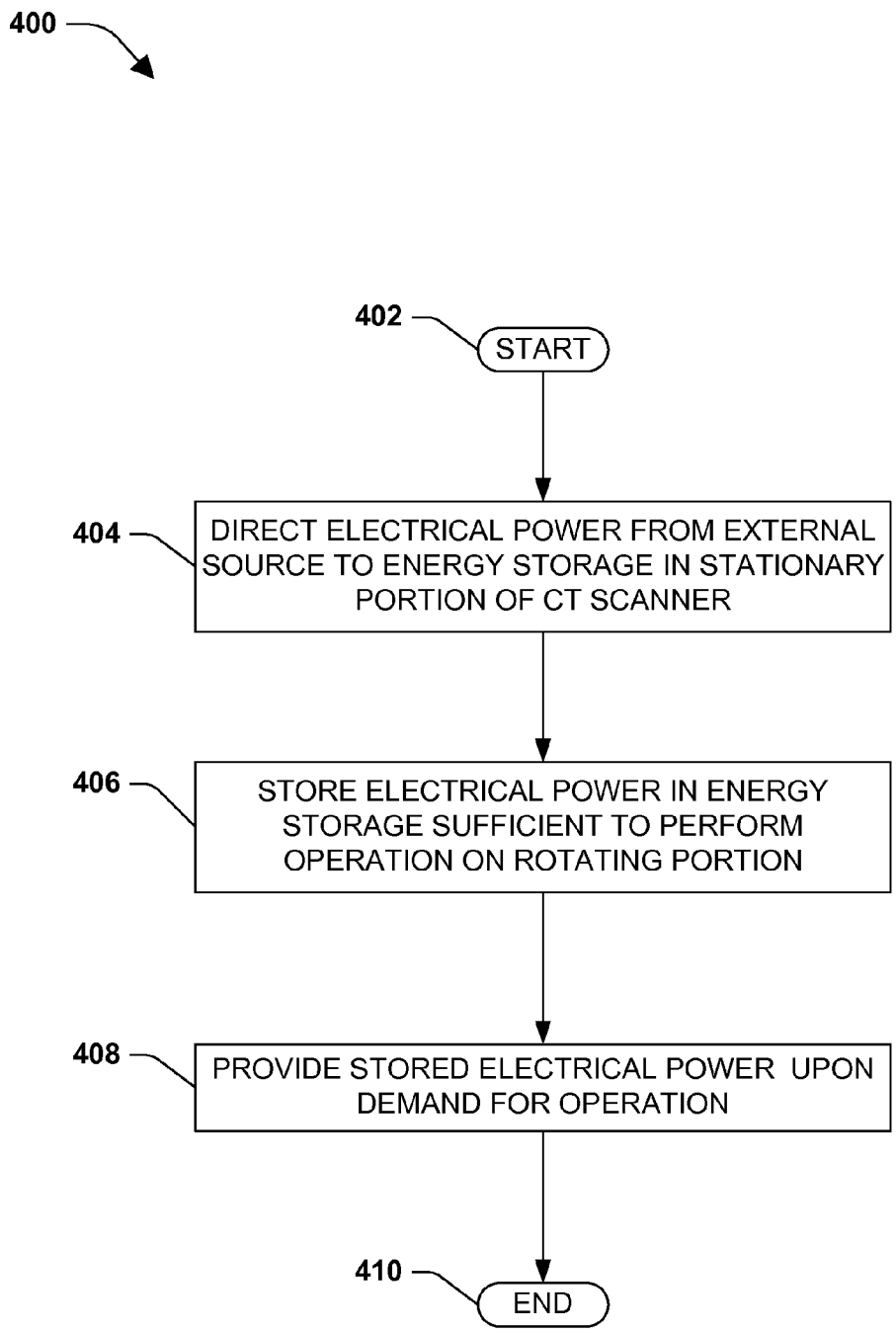
FIG. 4 is a flow diagram of an example method for providing electrical power using an energy storage component as provided herein.

FIG. 4 is a flow diagram illustrating an example method 400 wherein an energy storage component is utilized for providing electrical power for an operation on a rotating portion of a computed tomography (CT) scanning apparatus. The example method 400 begins at 402 and involves directing electrical power from an external source to an energy storage component that is disposed in a stationary portion of the CT scanning apparatus (or external to the CT system or stationary portion thereof), at 404. For example, the CT apparatus can comprise the energy storage component, and may be plugged into an electrical outlet (e.g., mains supply, such as 120 VAC in the U.S.) providing single-phase electrical power, or connected with a dedicated three-phase power supply. Once connected, in this example, electrical power from the external source (e.g., mains outlet or dedicated service) can be directed to the energy storage component in the stationary portion of the CT apparatus.

In one aspect, the stationary portion of a CT scanning apparatus can comprise any portion of the CT apparatus or system that does not rotate, such as for a scanning operation. For example, a CT scanner may be situated in a dedicated scanning room, such as in a clinic or hospital, that comprises scan computing components, an examination surface (e.g., separate from the CT unit) and/or other components used to generate imaging or other information from a scan. In this aspect, in this example, these components in the room used for scanning purposes may comprise the stationary portion of the CT scanning apparatus. In one embodiment, the energy storage component may be disposed in any part of the stationary portion of the CT scanning apparatus, such as operably coupled with the external source, so that electrical power can be directed to it.

At 406 in the example method 400, the electrical power from the external source is stored in the energy storage component, which is sufficient to perform the operation on the rotating portion of the CT scanning apparatus. For example, x-ray generation for a scanning operation can utilize up to 45 kW of electrical power, such as for a medical-type CT scan. Therefore, in order to provide sufficient power for x-ray generation (e.g., by an x-ray tube), for example, electrical power is stored in the energy storage component so that when the operation calls for power the sufficient amount is released by the energy storage component.

That is, for example, more electrical power may need to be stored in the energy storage component than is called for by the operation, as capacitors and/or batteries may not be able to release all of the electrical power stored therein for any given operation. Further, an amount of electrical power can be stored in the electrical storage component that may be sufficient for any operation performed on the rotating and/or stationary portions of the CT apparatus, singly or in combination, and merely a portion or the electrical power may be called for an operation in the CT apparatus.

For example, during a scanning operation, x-rays may be generated for the scan while the gantry rotates around an object (e.g., targeted for the scan) and the detector array detects photons and converts them to current, which are converted into an image for the scan. In this example, sufficient electrical power can be stored in the energy storage component that allows for this combination of operations to be performed concurrently, or substantially concurrently. Additionally, as an example, merely enough power may be called to be able to move the examination surface on which the object is disposed, such as to move the object into a scanning position.

At 408 in the example method 400, the stored electric power is provided upon demand for the operation. For example, when electrical power is called for a particular operation (e.g., CT scan, image computing, gantry rotation, detector operation, examination surface movement) sufficient electrical power is released from the energy storage component to perform the operation. Having provided the stored electrical power to perform the operation, the example method 400 ends at 410. In one example, stored electrical power may be provided in conjunction with power from a dedicated power source, where the combination provides power sufficient to perform one or more operations in the CT system.

Figure 5:
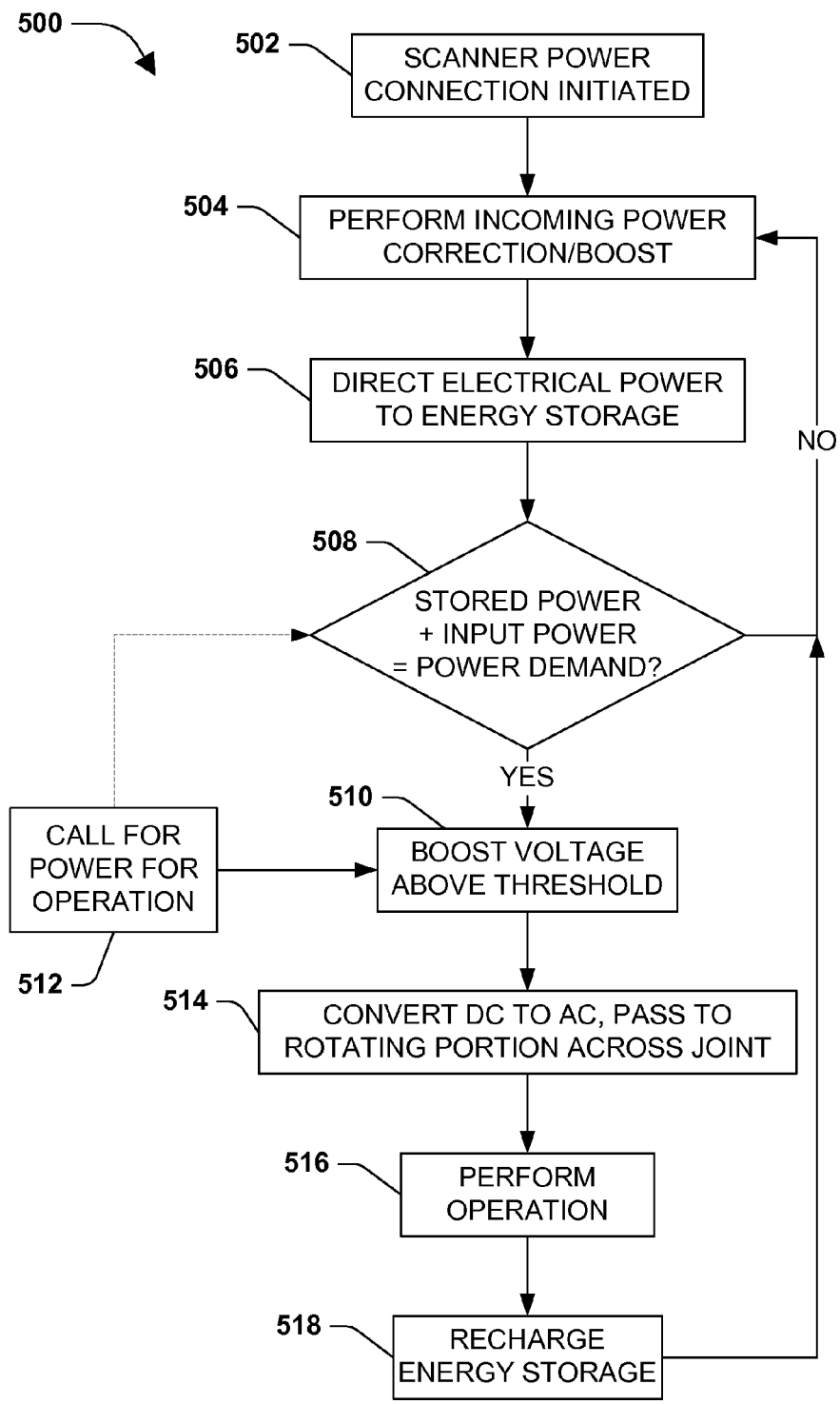
FIG. 5 is a flow diagram of an example method for performing an operation in a scanner as provided herein.

FIG. 5 is a flow diagram illustrating an example method 500 of utilizing an energy storage component for providing power in a CT system. At 502, a power connection is initiated for a CT scanning apparatus. For example, one or more electrical connections (e.g., power lines) for the CT apparatus may be plugged into existing mains outlets. In one embodiment, the techniques described herein provide for the CT apparatus to draw electrical power from typical electrical outlets, where the electrical supply provides general mains power (e.g., 120 VAC in the US). That is, for example, where a scanning operation, such as for a medical-type scan, requires more power than can be provided by a mains supply, the techniques described herein can provide for sufficient electrical power to perform the CT scan even when connected to a mains supply.

At 504, incoming electrical power from the external source can optionally be boosted. In one embodiment, where the energy storage component comprises one or more batteries, a boosting rectifier, for example, can be used to boost voltage from the external source above a desired threshold for storage in the energy storage component. For example, in order to store a sufficient amount of electrical power in the energy storage component when it comprises batteries for storing the electricity, the source electrical power may need to be at an appropriate voltage level, such as to fully charge the batteries. In this embodiment, boosting the voltage level can provide for more efficient use of the batteries (e.g., by fully charging them), thereby allowing fewer and/or smaller sized batteries to be utilized in the energy storage component, which can, among other things, save on costs.

Further, at 504, in one embodiment, the incoming electrical power from the external source can be corrected, such as by converting an incoming alternating current (AC) to direct current (DC). In this embodiment, the energy storage component may store electrical power in DC, whereas the external source may provide AC as the input power. Therefore, a rectifier, for example, can be used to convert the incoming AC to DC for storage. At 506, the optionally corrected and/or boosted electrical power is directed to the energy storage component for storage.

In one embodiment, the stored electric power may be provided upon demand to perform a CT operation, where the stored electric power may be combined with the external source electric power to provide sufficient electrical power to perform the operation. That is, for example, where the operation (e.g., scan) requires at least 'X' amount of power, and the external source can provide 'Y' amount of power, the energy storage component can store enough electrical power to provide 'X-Y' power upon demand (e.g., the scan requires 45 kW, the external source provides 4 kW, therefore the energy storage component provides 41 kW). Accordingly, at 508, a determination can be made (e.g., by a stored electrical power meter component) as to whether the energy storage component has sufficient stored electrical power to combine with the input source power to perform the operation. If the energy storage component does not have a desired amount of stored power (NO at 508), incoming electrical power can be corrected and/or boosted, at 504, and directed to the energy storage component, at 506, until the desired amount is stored.

In one embodiment, the desired amount of stored electrical power may be determined by a called operation, at 512. For example, an operation (e.g., on the rotating and/or stationary portions of the CT apparatus) may require a certain level of power. In one embodiment, a charge period can be configured that provides for the energy storage component to be charged with electrical power that is sufficient to perform the operation, such as where the stored electrical power is used to perform the operation alone, or when the stored electrical power is combined with the electrical power from the external power source. In this embodiment, performance of the operation, such as a CT scanning operation, can be mitigated during the charge period. That is, for example, the operation may not be performed until a desired level of electrical power is stored.

If enough electrical power is stored in the energy storage component to perform one or more CT operations, alone or in combination with the external source, (YES at 508) power for the operation(s) can be called, at 512. At 510, the voltage of the electrical power provided by the energy storage component can optionally be boosted above a desired voltage level threshold. In one embodiment, where the energy storage component comprises one or more capacitors, a boosting inverter can be used to boost voltage from the energy storage component above the desired threshold for the operation. For example, when electrical power is released from capacitors the voltage of the released power drops as the electrical power is released. Therefore, in this example, the voltage of the electrical power released from the energy storage component can be boosted to maintain a substantially constant level.

At 514, electrical power that is released from the energy storage component for the operation is converted from DC to AC. Further, in one embodiment, a non-contacting power transmission rotary joint can be used to provide an electrical connection between the stationary portion and the rotating portion of the CT scanning apparatus. At 514, the stored electrical power can be transmitted from the stationary portion to the rotating portion of the CT scanning apparatus across the non-contacting power transmission rotary joint.

At 516, the operation can be performed on the rotating portion of the CT apparatus, such as a scanning operation; and at 518, the energy storage component can be recharged. For example, in medical-type CT scanning, the CT apparatus is utilized in a periodic duty-cycle, where scans are typically performed periodically (e.g., a patient is scanned, and then another patient is brought in to be scanned). In a period between scans, for example, the incoming power from the external source can recharge the energy storage component in time for the next operation.

Figure 6:
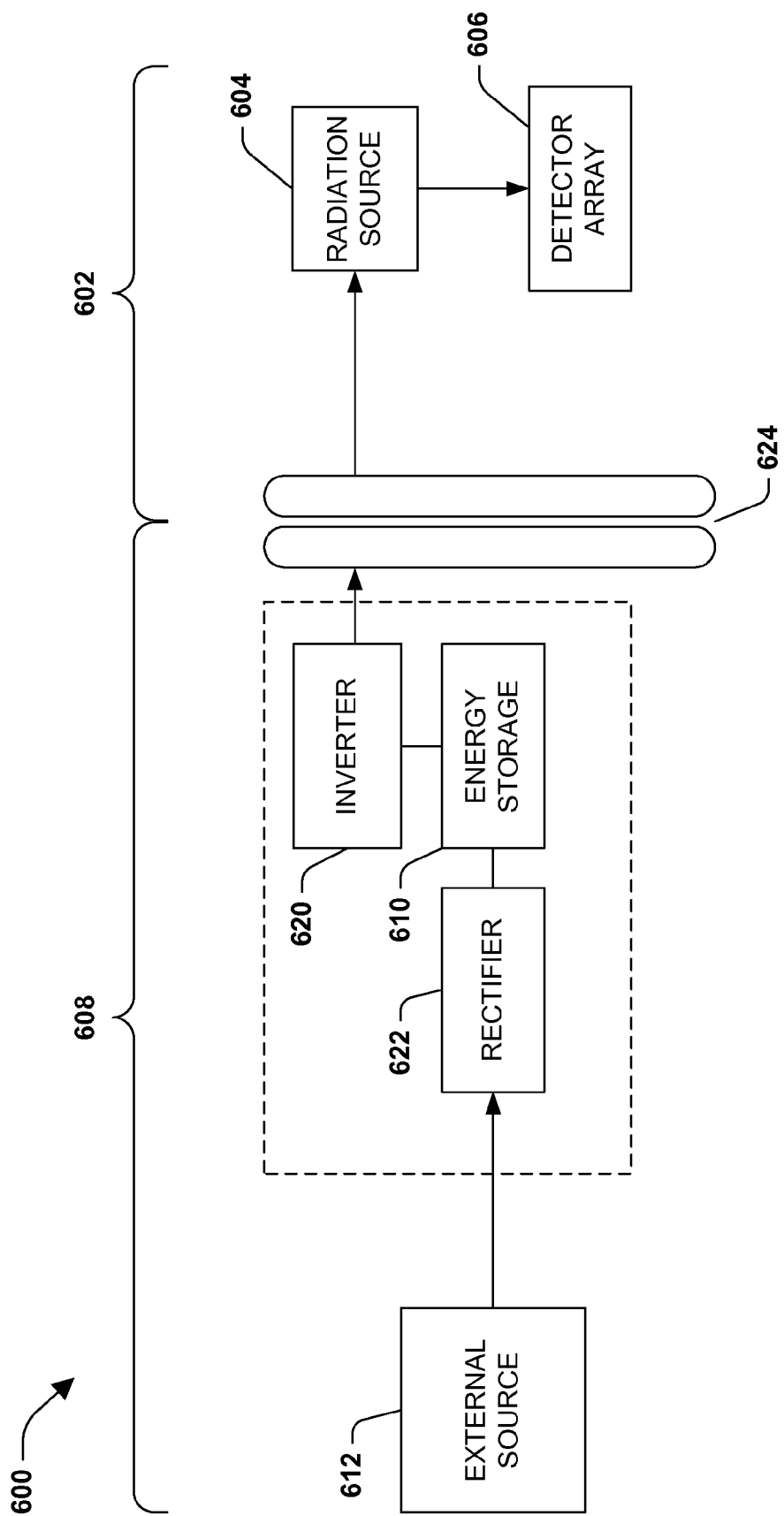
FIG. 6 is a component diagram illustrating an example implementation of a power management system as provided herein.

FIG. 6 is a component diagram of an alternate embodiment of an example system 600 configured to perform radiography scanning wherein an energy storage component is implemented. A rotating portion 602 of the example system 600 comprises a radiation source subsystem 604 that is configured to emit radiation as at least part of a scan operation. Further, the rotating portion 602 of the example system 600 comprises a detector array 606 that detects the emitted radiation during the scan operation. For example, the rotating portion 602 in this alternate embodiment can comprise a rotating gantry (e.g., 106 of FIG. 1), which rotates around an object subjected to a scanning operation while emitting radiation through the object, and detecting attenuated radiation to generate an image for the object.

A stationary portion 608 of the example system 600 comprises an energy storage component 610 that stores electrical power from an external source 612, which is applied to the energy storage component 610 during a charge period. That is, for example, the energy storage component 610 can be charged by electrical power from the external source 612 during a charging period. Further, the electrical power from the external source 612 is generally not sufficient to perform the scan operation on the rotating portion 602 alone. Accordingly, the energy storage component 610 provides stored electrical power for the scan operation, and this power may be provided upon demand. A combination of electrical power from the energy storage component 610 and the external source 612 is sufficient to perform the scan operation on the rotating portion 602.

In one embodiment, the stationary portion 608 can further comprise an inverter 620, between the energy storage component 610 and the rotating portion 602. In this embodiment, the inverter 620 can boost voltage from the energy storage component 610 above a desired threshold (e.g., to maintain a constant voltage level while draining the energy storage component 610) for the operation and/or convert direct current (DC) from the energy storage component 610 to alternating current (AC) for the operation on the rotating portion 602.

In one embodiment, the stationary portion 608 can further comprise a rectifier 622, between the external source 612 and the energy storage component 610. The rectifier 622 can boost voltage from the external source above a desired threshold (e.g., to raise the voltage to a level that helps completely charge batteries in the energy storage component 619) for energy storage in the energy storage component 610 and/or convert AC from the external source 612 to DC for the energy storage component 610.

In the example embodiment 600, a non-contacting power transmission rotary joint 624 is disposed between the stationary portion 608 and the rotating portion 602 to provide a conduit for high frequency electrical power from the inverter 620 to the rotating portion 602. That is, for example, the non-contact power transmitter 624 can transfer high frequency AC (e.g., and data) without direct contact (e.g., 80-100 kHz).

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A computed tomography (CT) scanning apparatus comprising:
   an energy storage component disposed in a stationary portion of the CT scanning apparatus, and configured to
      receive electrical power supplied from an external source,
      store the electrical power, and
      provide at least some of the stored electrical power for an operation on a rotating portion of the CT scanning apparatus upon demand, wherein the stored electrical power provided by the energy storage component comprises power sufficient to perform the operation.

2. The CT scanning apparatus of claim 1, wherein the external source is configured to supply single-phase alternating current (AC).

3. The CT scanning apparatus of claim 1, wherein the CT scanning apparatus is purposed for periodic duty cycle utilization.

4. The CT scanning apparatus of claim 1, comprising an inverter configured to convert direct current (DC) from the energy storage component to alternating current (AC) for the operation.

5. The CT scanning apparatus of claim 4, wherein the inverter comprises a preregulation component configured to boost voltage from the energy storage component above a desired threshold for the operation.

6. The CT scanning apparatus of claim 4, wherein the inverter is disposed in the stationary portion of the CT scanning apparatus between the energy storage component and an electrical connection to the rotating portion of the CT scanning apparatus.

7. The CT scanning apparatus of claim 1, comprising a non-contacting power transmission rotary component disposed between the stationary portion and the rotating portion of the CT scanning apparatus, the non-contacting power transmission rotary component configured to provide a conduit for electrical power to the rotating portion of the CT scanning apparatus.

8. The CT scanning apparatus of claim 1, comprising a rectifier component disposed between the external source and the energy storage component, the rectifier component configured to condition the electrical power supplied from the external source for storage in the energy storage component.

9. The CT scanning apparatus of claim 1, wherein the energy storage component comprises one or more of:
   one or more batteries configured to store the electrical power; or one or more capacitors configured to store the electrical power.

10. The CT scanning apparatus of claim 1, wherein the operation on the rotating portion of the CT scanning apparatus comprises one or more of:
   emitting radiation from a radiation source;
   rotating a gantry;
   moving an examination surface;
   operating a detector array; or
   operating a data acquisition component.

11. A method for providing electrical power for an operation on a rotating portion of a computed tomography (CT) scanning apparatus, comprising:
   receiving electrical power from an external source at an energy storage component disposed in a stationary portion of the CT scanning apparatus;
   storing electrical power in the energy storage component, the stored electrical power sufficient to perform the operation on the rotating portion of the CT scanning apparatus; and
   providing, upon demand, at least some of the stored electrical power for the operation on the rotating portion of the CT scanning apparatus.

12. The method of claim 11, wherein the providing is performed during rotation of the rotating portion of the CT scanning apparatus during a CT scanning operation.

13. The method of claim 11, comprising one or more of:
   using a boosting inverter to boost voltage from the energy storage component above a desired threshold for the operation; or
   using a boosting rectifier to boost voltage from the external source above a desired threshold for storage in the energy storage component.

14. The method of claim 11, comprising using a non-contacting power transmission rotary component to provide an electrical connection between the stationary portion and the rotating portion of the CT scanning apparatus.

15. The method of claim 11, comprising configuring a charge period wherein the energy storage component is charged with electrical power sufficient to perform the operation.

16. The method of claim 15, comprising mitigating performance of a CT scanning operation during the charge period.

17. The method of claim 11, comprising converting the electrical power from the external source from alternating current to direct current prior to storing the electrical power in the energy storage component.

18. A computed tomography (CT) system, comprising:
   a radiation source configured to emit radiation;
   a detector array configured to detect a portion of emitted radiation that traversed an object being scanned;
   a rotating portion to which the radiation source and the detector array are coupled, and configured to rotate the radiation source and the detector array relative to the object while the object is being scanned; and
   a stationary portion comprising an energy storage component configured to store electrical power applied to the energy storage component and provide at least some of the stored electrical power for an operation on the rotating portion of the CT system, wherein the stored electrical power provided by the energy storage component comprises power sufficient to perform the operation.

19. The CT system of claim 18, wherein the stationary portion comprises one or more of:
   an inverter disposed between the energy storage component and the rotating portion; or
   a rectifier disposed between an external source that applied the electrical power to the energy storage component and the energy storage component.

20. The CT system of claim 18, wherein the operation comprises emitting the radiation from the radiation source.

* * * * *

UNITED STATES PATENT AND TRADEMARK OFFICE
CERTIFICATE OF CORRECTION

PATENT NO. : 8,379,797 B2  
APPLICATION NO. : 12/845988  
DATED : February 19, 2013  
INVENTOR(S) : Daniel Abenaim and Adrian Delforge Page 1 of 1

It is certified that error appears in the above-identified patent and that said Letters Patent is hereby corrected as shown below:

In the Claims:

Claim 1, Column 14, Line 25: Add a ":" after the words "and configured to"

Signed and Sealed this
Twenty-eighth Day of May, 2013

Teresa Stanek Rea
*Acting Director of the United States Patent and Trademark Office*